(12) United States Patent
Iizuka et al.

(10) Patent No.: US 6,844,354 B1
(45) Date of Patent: Jan. 18, 2005

(54) AGENT FOR PROPHYLAXIS AND TREATMENT OF INTERSTITIAL PNEUMONIA AND PULMONARY FIBROSIS

(75) Inventors: Kunihiko Iizuka, Takasaki (JP); Kunio Dobashi, Maebashi (JP); Masayoshi Uehata, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/937,221

(22) PCT Filed: Mar. 21, 2000

(86) PCT No.: PCT/JP00/01728

§ 371 (c)(1),
(2), (4) Date: Jul. 18, 2002

(87) PCT Pub. No.: WO00/57913

PCT Pub. Date: Oct. 5, 2000

(30) Foreign Application Priority Data

Mar. 25, 1999 (JP) .............................. 11/081072

(51) Int. Cl.[7] ..................... A61K 31/435; A61K 31/445; A61K 31/44
(52) U.S. Cl. ........................ 514/300; 514/302; 514/303; 514/252; 514/253; 514/352
(58) Field of Search ................................ 514/300, 302, 514/303, 252, 253, 352

(56) References Cited

U.S. PATENT DOCUMENTS

| 5,880,156 A | 3/1999 | Lang et al. ................ 514/618 |
| 5,906,819 A | 5/1999 | Kaibuchi et al. .......... 424/94.5 |

FOREIGN PATENT DOCUMENTS

| EP | 519354 | 12/1992 |
| EP | 0 519 354 | 12/1992 |
| EP | 784980 | 7/1997 |
| EP | 0 784 980 | 7/1997 |
| EP | 893437 | 1/1999 |
| EP | 0 893 437 | 1/1999 |
| EP | 0 956 865 | 11/1999 |
| JP | 61-158983 | 7/1986 |
| JP | 2-290821 | 11/1990 |
| JP | 6-345643 | 12/1994 |
| JP | 10-113187 | 5/1998 |
| JP | 10-218768 | 8/1998 |
| WO | 98/06433 | 2/1998 |
| WO | 98-47892 | 10/1998 |
| WO | 00/09162 | 2/2000 |

OTHER PUBLICATIONS

Database BIOSIS Online abstract of Kunitake et al., "Expression of p53, p21 (Waf1/Cip1/Sdi1) and Fas antigen in collagen vascular and granulamatous lung diseases", European Respiratory Journal, vol. 12, No. 4, Oct., 1998.

Database BIOSIS Online abstract of Kuwano Kazuyoshi et al., "P21–Waf1/Cip1/Sdi1 and p53 expression in association with DNA strand breaks in idiopathic pulmonary fibrosis", American Journal of Respiratory and Critical Care Medicine, vol. 154, No. 2, part 1, 1996, pp. 477–483.

Database BIOSIS Online abstract of Rauf Brandt et al., "Serum Oncoproteins and Growth Factors in Asbestosis and Silicosis Patients", International Journal of Cancer, vol. 50, No. 6, 1992, pp. 881–885.

Database BIOSIS Online abstract of K. Kawano et al., "The roles of apoptosis in lung injury and fibrosis", Journal of the Japanese Respiratory Society, vol. 36, No. 9., Sep. 1998, pp. 739–744.

*Primary Examiner*—Bernard Dentz
(74) *Attorney, Agent, or Firm*—Wenderoth, Lind & Ponack, L.L.P.

(57) ABSTRACT

An agent for the prophylaxis and treatment of interstitial pneumonia and pulmonary fibrosis, which contains a compound having a Rho kinase inhibitory activity, particularly an agent for the prophylaxis and treatment of interstitial pneumonia and pulmonary fibrosis, which contains a compound of the formula (I)

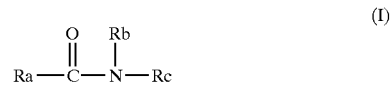

(I)

wherein each symbol is as defined in the specification, as the compound having a Rho kinase inhibitory activity, is provided.

8 Claims, 3 Drawing Sheets

AGENT FOR PROPHYLAXIS AND TREATMENT OF INTERSTITIAL PNEUMONIA AND PULMONARY FIBROSIS

This application is a 371 of PCT/JP00/01728 filed Mar. 21, 2000.

TECHNICAL FIELD

The present invention relates to an agent for the prophylaxis and treatment of interstitial pneumonia and pulmonary fibrosis. More specifically, the present invention relates to an agent for the prophylaxis and treatment of interstitial pneumonia and pulmonary fibrosis, which comprises a compound having a Rho kinase inhibitory activity as an active ingredient.

BACKGROUND ART

Interstitial pneumonia is an inflammation of lung stroma, which means an inflammation of alveolar wall and peripheral supporting tissue. While it includes local one and diffuse one, interstitial pneumonia generally means diffuse interstitial pneumonia, including acute type and chronic type. Histologically, it is classified into five types of UIP (usual or classical interstitial pneumonia), BIP (obstructive bronchiolar interstitial pneumonia), DIP (desquamative interstitial pneumonia), LIP (lymphoid interstitial pneumonia) and GIP (giant cell interstitial pneumonia). Those having an unknown cause are called idiopathic interstitial pneumonia (XIP) in Japan and idiopathic pulmonary fibrosis (IPF) in US and Europe. Those having a known cause include pneumoconiosis, hypersensitivity pneumonitis, radiation pneumonitis, infection disease and the like. The disease sometimes accompanies a systemic dusease, such as sarcoidosis, histiocytosis X, collagen disease and the like. Clinically, dry coughing, exertional dyspnea, fever, clubbing of finger, cyanosis and the like are observed. One associated with systemic disease shows other systemic symptoms. The disease shows Velcro rale (fine crackle) by chest auscultation, ground glass opacity in an early stage, then fine particle-like shadow, and orbicular shadow and honeycomb shadow as the disease progresses, by chest X-ray image. By ventilatory function test, restrictive ventilatory defect, diffusion disturbance and hypoxemia are observed. It is an intractable disease with poor prognosis that shows fibrosis or honey cone lung as the final image.

Pulmonary fibrosis in interstitial pneumonia is pathologically alveolar septal tylosis, mainly characterized by growth of type II alveolar epithelial cells and fibroblast, and an increase in the collagen fibers produced by fibroblast. Its etiology is not certain but involvement of various cytokines is postulated. That is, known cellular groups involved therein are fibroblast, smooth muscle cell, hematocyte-derived macrophage, lymphocyte, neutrophile, acidocyte and basocyte, all of which constituting the mesenchymal cell, and alveolar epithelial cell, respiratory epithelial cell, vascular endothelial cell and the like as epidermic cells. These cells are activated by inflammatory stimulaion and the like and express various cytokines and the like, and induce changes in adhesion molecules. By these, pulmonary tissues are damaged, which triggers proliferation of type II alveolar epithelial cell and fibroblast, thereby advancing fibrosis.

Pulmonary fibrosis is a disease where diffuse fibroplasia of alveolar wall is observed, and is mainly characterized by dry coughing and exertional dyspnea. The name of pulmonary fibrosis means the end of interstitial pneumonia in a narrow sense, but in a wide sense, it means concomitant presence of pulmonary fibrosis in a narrow sense and interstitial pneumonia. Any interstitial pneumonia can cause this disease. It shows noticeable diffuse honeycomb shadow and pulmonary atrophy by X-ray chest image, and restrictive ventilatory defect, diffusion disturbance and hypoxemia are found by a ventilatory function test.

On the other hand, an antitumor agent, bleomycin, is known to cause, as a side effect, diffuse alveolar damage in the acute stage, and interstitial pneumonia and pulmonary fibrosis in the chronic stage. In an animal test, too, the administration of bleomycin shows initial images of interstitial pneumonia in the acute stage, and tylosis of alveolar wall, growth of type II alveolar cells and fibroblasts in the chronic stage, and many studies have been made as a model of human interstitial pneumonia and pulmonary fibrosis.

The conventional main therapy of such interstitial pneumonia and pulmonary fibrosis is administration of a steroid drug against active symptoms. This agent does not bring about a cure of the disease, but suppression of activity of the disease and stabilization of disease state. Thus, the utility of the drug is open to question. Moreover, a weight loss due to the steroid drug administration frequently induces acute exacerbation, which, in rare instances, is known to result in a death, and administration of a steroid drug is considered to be ineffective particularly in chronic cases. In the case of sarcoidosis, it is considered to even aggravate the long term prognosis.

Therefore, the creation of a drug aiming at a cure of the disease itself of the above-mentioned interstitial pneumonia, pulmonary fibrosis and the like has been awaited.

As a compound having a Rho kinase inhibitory activity, a compound of the formula (I) to be mentioned later has been reported (WO98/06433). Certain isoquinolinesulfonamide derivative and isoquinoline derivative are also reported to show a Rho kinase inhibitory activity (WO98/06433 and Naunyn-Schmiedeberg's Archives of Pharmacology 385(1) Suppl., R219, 1998).

The pharmaceutical use of a compound having a Rho kinase inhibitory activity is disclosed in WO98/06433, and described to be widely useful as a therapeutic agent of hypertension, a therapeutic agent of angina pectoris, a cerebrovascular spasm suppressant, a therapeutic agent of asthma, a therapeutic agent of peripheral circulatory disturbance, a premature delivery preventive, a therapeutic agent of arterial sclerosis, an anticancer drug, an anti-inflammatory agent, an immunosuppressant, a therapeutic agent of autoimmune diseases, an anti-AIDS agent, a therapeutic agent of osteoporosis, a therapeutic agent of retinopathy, a cerebral function improver, a contraceptive drug, and a gastrointestinal tract infection preventive. On the other hand, WO98/06433 does not teach its usefulness for the prevention and treatment of interstitial pneumonia and pulmonary fibrosis, or a description to suggest such effect.

Furthermore, the compound of formula (I) has been already known to be useful as an agent for the prophylaxis and treatment of disorders of circulatory organs such as coronary, cerebral, renal, peripheral artery and the like (e.g., a therapeutic agent of hypertension, a therapeutic agent of angina pectoris, a therapeutic agent of renal and peripheral circulation disorder, a suppressive agent of cerebrovascular contraction and the like), which is potent and long lasting, and also as a therapeutic agent of asthma (JP-A-62-89679, JP-A-3-218356, JPA-4-273821, JP-A-5-194401, JP-A-6-41080 and WO95/28387).

The isoquinolinesulfonamide derivative described in the above-mentioned WO98/06433 is known to be effective as a vasodilating agent, a therapeutic agent of hypertension, a cerebral function improver, an anti-asthma agent, a heart protecting agent, a platelet aggregation inhibitor, a therapeutic agent of neurologic manifestation, an anti-inflammatory agent, an agent for the prevention and treatment of hyperviscosity syndrome, a therapeutic agent of glaucoma, a diminished tension agent, a motor paralysis improver of cerebral thorbmbosis, an agent for prevention and treatment of virus infection and transcriptional control factor inhibitor (JP-A-57-200366, JP-A-61-227581, JP-A-2-256617, JP-A-4-264030, JP-A-6-56668, JP-A-6-80569, JP-A-6-293643, JP-A-7-41424, JP-A-7-277979, WO97/23222, JP-A-9-227381, JP-A-10-45598 and JP-A-10-87491).

Moreover, the isoquinoline derivative described in the above-mentioned publication (Naunyn-Schmiedeberg's Archives of Pharmacology 385(1) Suppl., R219, 1998) is known to be useful as an agent for the prevention and treatment of brain tissue disorder due to vasospasm (WO97/28130).

However, these compounds having Rho kinase inhibitory activity are not disclosed to be useful for prophylaxis and treatment of interstitial pneumonia and pulmonary fibrosis, and there is no description suggestive of such usefulness.

DISCLOSURE OF THE INVENTION

The present invention aims at solving the above-mentioned problems and provides a novel agent for the prophylaxis and treatment of interstitial pneumonia and pulmonary fibrosis, which is superior in a prophylactic and therapeutic effect on interstitial pneumonia and pulmonary fibrosis.

The present inventors have conducted intensive studies and found that a compound having a Rho kinase inhibitory activity has an effect of the prevention and treatment of interstitial pneumonia and pulmonary fibrosis, and that it is useful for the prophylaxis and treatment of interstitial pneumonia, which resulted in the completion of the present invention.

Accordingly, the present invention provides the following.
(1) An agent for the prophylaxis and treatment of interstitial pneumonia and pulmonary fibrosis, which comprises a compound having a Rho kinase inhibitory activity.
(2) The agent for the prophylaxis and treatment of interstitial pneumonia and pulmonary fibrosis of (1) above, wherein the compound having a Rho kinase inhibitory activity is an amide compound of the following formula (I)

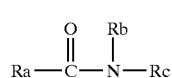

(I)

wherein
Ra is a group of the formula

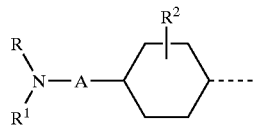

(a)

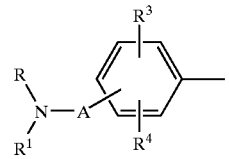

(b)

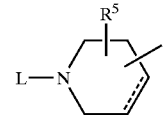

(c)

in the formulas (a) and (b),

R is hydrogen, alkyl, or cycloalkyl, cycloalkylalkyl, phenyl or aralkyl, which optionally has a substituent on the ring, or a group of the formula

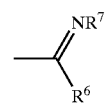

(d)

wherein $R^6$ is hydrogen, alkyl or formula: $-NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

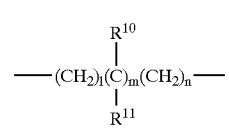

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

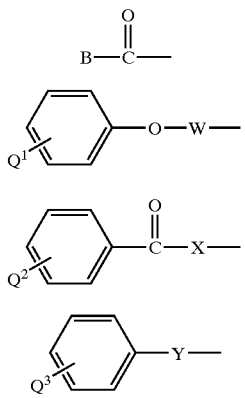

(f)

(g)

(h)

(i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(3) The agent for the prophylaxis and treatment of interstitial pneumonia and pulmonary fibrosis of (1) or (2) above, wherein the compound having a Rho kinase inhibitory activity is an amide compound of the following formula (I')

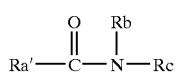

(I')

wherein

Ra' is a group of the formula

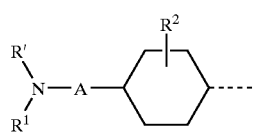

(a')

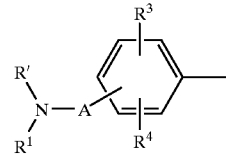

(b')

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

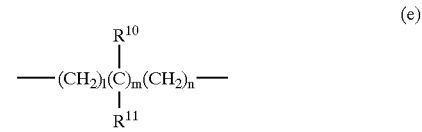

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(4) The agent for the prophylaxis and treatment of interstitial pneumonia and pulmonary fibrosis of (1) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

(5) The agent for the prophylaxis and treatment of interstitial pneumonia and pulmonary fibrosis of (1) above, wherein the compound having a Rho kinase inhibitory activity is (+)-trans-4-(1-aminoethyl)-1-(4-pyridylcarbamoyl)cyclohexane and/or a pharmaceutically acceptable acid addition salt thereof.

(6) A pharmaceutical composition for the prophylaxis and treatment of interstitial pneumonia and pulmonary fibrosis, which comprises a compound having a Rho kinase inhibitory activity and a pharmaceutically acceptable carrier.

(7) The pharmaceutical composition for the prophylaxis and treatment of interstitial pneumonia and pulmonary fibrosis of (6) above, wherein the compound having a Rho kinase inhibitory activity is an amide compound of the formula (I), an isomer thereof and/or a pharmaceutically acceptable acid addition salt thereof.

(8) The pharmaceutical composition for the prophylaxis and treatment of interstitial pneumonia and pulmonary fibrosis of (6) or (7), wherein the compound having a Rho kinase inhibitory activity is an amide compound of the formula (I'), an isomer thereof and/or a pharmaceutically acceptable acid addition salt thereof.

(9) The pharmaceutical composition for the prophylaxis and treatment of interstitial pneumonia and pulmonary fibrosis of (6) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

(10) The pharmaceutical composition for the prophylaxis and treatment of interstitial pneumonia and pulmonary fibrosis of (6) above, wherein the compound having a Rho kinase inhibitory activity is (+)-trans-4-(1-aminoethyl)-1-(4-pyridylcarbamoyl)cyclohexane and/or a pharmaceutically acceptable acid addition salt thereof.

(11) A method of the prophylaxis and treatment of interstitial pneumonia and pulmonary fibrosis, which comprises administering an effective amount of a compound having a Rho kinase inhibitory activity to a patient.

(12) The method of the prophylaxis and treatment of interstitial pneumonia and pulmonary fibrosis of (11) above, wherein the compound having a Rho kinase inhibitory activity is an amide compound of the formula (I), an isomer thereof and/or a pharmaceutically acceptable acid addition salt thereof.

(13) The method of the prophylaxis and treatment of interstitial pneumonia and pulmonary fibrosis of (11) or (12) above, wherein the compound having a Rho kinase inhibitory activity is an amide compound of the formula (I'), an isomer thereof and/or a pharmaceutically acceptable acid addition salt thereof.

(14) The method of the prophylaxis and treatment of interstitial pneumonia and pulmonary fibrosis of (11) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

(15) The method of the prophylaxis and treatment of interstitial pneumonia and pulmonary fibrosis of (11) above, wherein the compound having a Rho kinase inhibitory activity is a (+)-trans-4-(1-aminoethyl)-1-(4-pyridylcarbamoyl)cyclohexane, and/or a pharmaceutically acceptable acid addition salt thereof.

(16) Use of a compound having a Rho kinase inhibitory activity for the production of an agent for the prophylaxis and treatment of interstitial pneumonia and pulmonary fibrosis.

(17) The use of (16) above, wherein the compound having a Rho kinase inhibitory activity is an amide compound of the following formula (I), an isomer thereof and/or a pharmaceutically acceptable acid addition salt thereof.

(18) The use of (16) or (17) above, wherein the compound having a Rho kinase inhibitory activity is an amide compound of the following formula (I'), an isomer thereof and/or a pharmaceutically acceptable acid addition salt thereof.

(19) The use of (16) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

(20) The use of (16) above, wherein the compound having a Rho kinase inhibitory activity is a (+)-trans-4-(1-aminoethyl)-1-(4-pyridylcarbamoyl)cyclohexane, and/or a pharmaceutically acceptable acid addition salt thereof.

(21) A commercial package comprising a pharmaceutical composition for the prophylaxis and treatment of interstitial pneumonia and pulmonary fibrosis of any of (6) to (10) above, and a written matter associated therewith, the written matter stating that the pharmaceutical composition can or should be used for the prophylaxis and treatment of interstitial pneumonia and pulmonary fibrosis.

DETAILED DESCRIPTION OF THE INVENTION

Figure 1:
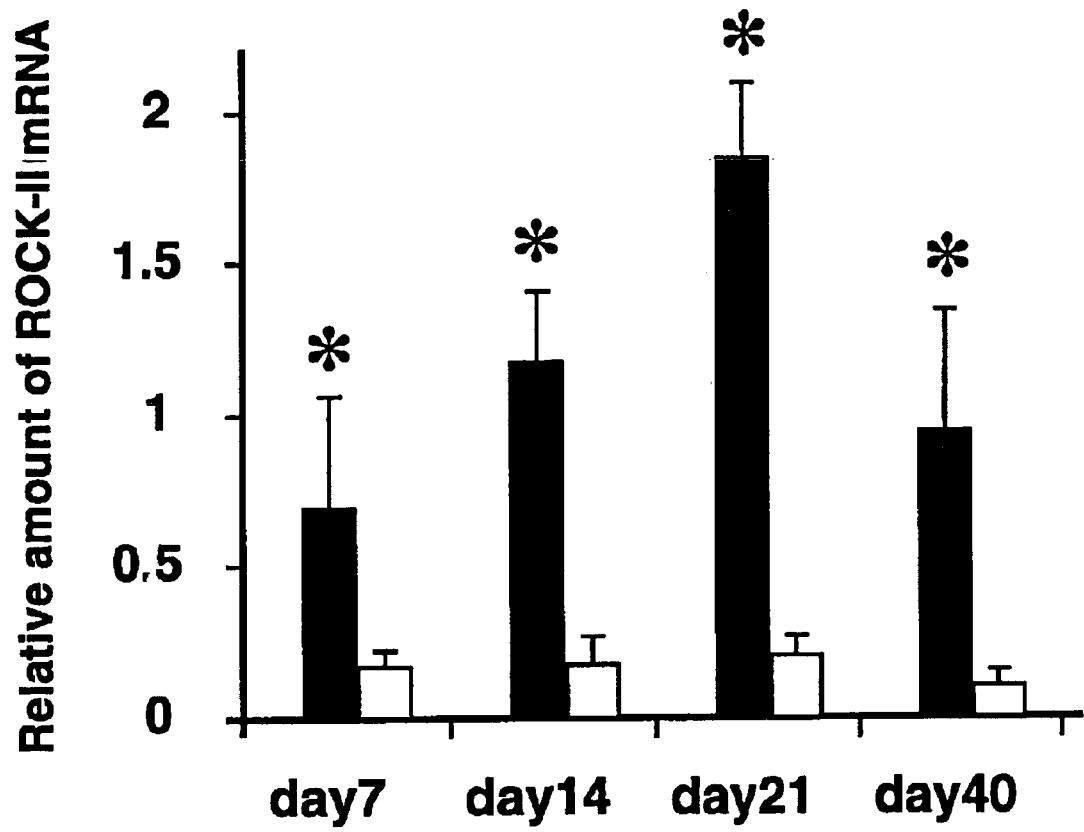
FIG. 1 is a graph showing the expression amount of a ROCK-II gene in a model with bleomycin-induced interstitial pneumonia (pulmonary fibrosis), wherein the axis of ordinates shows relative expression amount of the ROCK-II gene (ROCK-II mRNA/GAPDH mRNA), the axis of abscissas shows the time (days) after bleomycin administration, □ shows a bleomycin non-administration group and ■ shows a bleomycin administration group (total amount of administration 200 mg/kg), (n=4, *p<0.05).

In the present invention, by the "interstitial pneumonias" is meant an inflammation of lung stroma, which refers to an inflammation of alveolar wall and peripheral supporting tissue. While it includes local one and diffuse one, interstitial pneumonia generally refers to diffuse interstitial pneumonia, including acute type and chronic type. Histologically, it is classified into 5 types of UIP (usual or classical interstitial pneumonia), BIP (obstructive bronchiolar interstitial pneumonia), DIP (desquamative interstitial pneumonia), LIP (lymphoid interstitial pneumonia) and GIP (giant cell interstitial pneumonia). The disease whose cause is unknown is referred to as idiopathic interstitial pneumonia (IIP). One with clarified cause is referred to as pneumoconiosis, hypersensitivity pneumonitis, radiation pneumonitis, infection disease and the like. The disease may accompany a systemic disease such as sarcoidosis, histiocytosis X, collagen disease and the like. Clinically, dry coughing, exertional dyspnea, fever, clubbing of finger, cyanosis and the like are observed, and one accompanying a systemic disease may show other systemic symptoms. The disease shows Velcro rale (fine crackle) by chest auscultation, ground glass opacity in an early stage, then fine particle-like shadow, and orbicular shadow and honeycomb shadow as the disease progresses, by chest X-ray image. By ventilatory function test, restrictive ventilatory defect, diffusion disturbance and hypoxemia are observed.

In the present invention, the pulmonary fibrosis means a disease where diffuse fibroplasias of the alveolar wall is found and the main symptoms are dry coughing and exertional dyspnea. While the name of pulmonary fibrosis means terminal interstitial pneumonia in a narrow sense, pulmonary fibrosis of the present invention refers to one in a wide sense, concurrently including pulmonary fibrosis in a narrow sense and interstitial pneumonia. Any interstitial pneumonia can cause this disease. In a chest X-ray image, diffuse honeycomb shadow and pulmonary atrophy are noticeable, and in a ventilatory function test, restrictive ventilatory defect, diffusion disturbance and hypoxemia are observed.

In the present invention, Rho kinase means serine/threonine kinase activated along with the activation of Rho. For example, ROKα (ROCKII: Leung, T. et al, J. Biol. Chem., 270, 29051–29054, 1995), p160 ROCK (ROKβ, ROCK-I: Ishizaki, T. et al, The EMBO J., 15(8), 1885–1893, 1996) and other proteins having a serine/threonine kinase activity are exemplified.

The compound having a Rho kinase inhibitory activity, which is used as an active ingredient in the present invention, may be any as long as it has a Rho kinase inhibitory activity. Specifically, there are mentioned amide compound, isoquinolinesulfonamide derivative and isoquinoline derivative described in the above-mentioned WO98/06433 and WO97/28130 [particularly Naunyn-Schmiedeberg's Archives of Pharmacology 385(1) Suppl., R219, 1998].

As the aforementioned amide compound, for example, a compound of the above-mentioned formula (I), particularly a compound of the formula (I'), are used. As the aforementioned isoquinolinesulfonic acid derivative, fasudil hydrochloride [hexahydro-1-(5-isoquinolinesulfonyl)-1H-1,4-diazepine] and the like are used. As the aforementioned isoquinoline derivative, hexahydro-1-[(4-methyl-5-isoquinolinyl)sulfonyl]-1H-1,4-diazepine dihydrochloride, (S)-(+)-hexahydro-2-methyl-1-[(4-methyl-5-isoquinolinyl) sulfonyl]-1H-1,4-diazepine hydrochloride, hexahydro-7-methyl-1-[(4-methyl-5-isoquinolinyl)sulfonyl]-1H-1,4-diazepine dihydrochloride, hexahydro-5-methyl-1-[(4-methyl-5-isoquinolinyl)sulfonyl]-1H-1,4-diazepine dihydrochloride, hexahydro-2-methyl-1-[(4-methyl-5-isoquinolinyl)sulfonyl]-1H-1,4-diazepine hydrochloride, (R)-(−)-hexahydro-2-methyl-1-[(4-methyl-5-isoquinolinyl) sulfonyl]-1H-1,4-diazepine hydrochloride, (R)-(+)-hexahydro-5-methyl-1-[(4-methyl-5-isoquinolinyl) sulfonyl]-1H-1,4-diazepine hydrochloride and the like are used.

Preferably, an amide compound of the formula (I), particularly preferably an amide compound of the formula (I'), is used.

In the present invention, one kind of a compound having a Rho kinase inhibitory activity may be used alone, or, where necessary, several kinds may be concurrently used.

In the present specification, each symbol of the formulas (I) and (I') is defined as follows.

Alkyl at R, R' and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl at R, R' and $R^1$ has 3 to 7 carbon atoms and is exemplified by cyclopropyl, cyclobutyl, cyclopentyl, cyclohexyl, cycloheptyl and the like.

Cycloalkylalkyl at R, R' and $R^1$ is that wherein the cycloalkyl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cyclopentylhexyl, cyclohexylhexyl, cycloheptylhexyl and the like.

Aralkyl at R, R' and $R^1$ is that wherein alkyl moiety is alkyl having 1 to 4 carbon atoms and is exemplified by phenylalkyl such as benzyl, 1-phenylethyl, 2-phenylethyl, 3-phenylpropyl, 4-phenylbutyl and the like.

The substituent of optionally substituted cycloalkyl, cycloalkylalkyl, phenyl and aralkyl on the ring at R, R' and $R^1$ is halogen (e.g., chlorine, bromine, fluorine and iodine), alkyl (same as alkyl at R, R' and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl at R, R' and $R^1$) or haloalkyl (alkyl at R, R' and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and R' or R' and $R^1$ in combination together with the adjacent nitrogen atom, which forms a heterocycle optionally having, in the ring, oxygen atom, sulfur atom or optionally substituted nitrogen atom is preferably a 5 or 6-membered ring and bonded ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R, R' and $R^1$.

Alkyl at $R^2$ is as defined for R, R' and $R^1$.

Halogen, alkyl, alkoxy and aralkyl at R3 and $R^4$ are as defined for R, R' and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is alkylamino having linear or branched alkyl having 1 to 6 carbon atoms. Examples thereof include methylamino, ethylamino, propylamino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzyl or the alkanoyl moiety is phenylalkanoyl having 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

Aralkylthio at $R^3$ and $R^4$ is that wherein the alkyl moiety is alkyl having 1 to 4 carbon atoms, which is exemplified by benzylthio, 1-phenylethylthio, 2-phenylethylthio, 3-phenylpropylthio, 4-phenylbutylthio and the like.

Alkoxycarbonyl at $R^3$ and $R^4$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Alkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R, R' and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1$–$C_4$ alkyl, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

Alkyl at $R^6$ is as defined for R, R' and $R^1$; alkyl at $R^8$ and $R^9$ is as defined for R, R' and $R^1$; and aralkyl at $R^8$ and $R^9$ is as defined for R, R' and $R^1$.

Alkyl at $R^7$ is as defined for R, R' and $R^1$ and aralkyl at $R^7$ is as defined for R, R' and $R^1$.

The group formed by $R^6$ and $R^7$ in combination, which forms a heterocycle optionally having, in the ring, oxygen atom, sulfur atom or optionally substituted nitrogen atom, is imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl, nitro, amino, phenyl, aralkyl and the like. As used herein, halogen, alkyl, alkoxy, haloalkyl and aralkyl are as defined for R, R' and $R^1$.

The substituent of the above-mentioned optionally substituted nitrogen atom is exemplified by alkyl, aralkyl, haloalkyl and the like. As used herein, alkyl, aralkyl and haloalkyl are as defined for R, R' and $R^1$.

Hydroxyalkyl at $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like.

Alkyl at $R^{10}$ and $R^{11}$ is as defined for R, R' and $R^1$; haloalkyl and alkoxycarbonyl at $R^{10}$ and $R^{11}$ are as defined for R, R' and $R^1$; aralkyl at $R^{10}$ and $R^{11}$ is as defined for R, R' and $R^1$.

Cycloalkyl formed by $R^{10}$ and $R^{11}$ in combination is the same as cycloalkyl at R, R' and $R^1$.

Alkyl at L is as defined for R, R' and $R^1$.

Aminoalky at L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl at L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

Carbamoylalkyl at L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl at L is linear or branched alkyl having 1 to 6 carbon atoms, which is substituted by phthalimide. Examples thereof include phthalimidomethyl, 2-phthalimidoethyl, 1-phthalimidoethyl, 3-phthalimidopropyl, 4-phthalimidobutyl, 5-phthalimidopentyl, 6-phthalimidohexyl and the like.

Alkyl at B is as defined for R, R' and $R^1$.

Alkoxy at B is as defined for R, R' and $R^1$.

Aralkyl at B is as defined for R, R' and $R^1$.

Aralkyloxy at B is as defined for $R^3$ and $R^4$.

Aminoalkyl at B is as defined for L.

Hydroxyalkyl at B is as defined for $R^{10}$ and $R^{11}$.

Alkanoyloxyalkyl at B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl at B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen at $Q^1$, $Q^2$ and $Q^3$ is as defined for R, R' and $R^1$.

Aralkyloxy at $Q^1$ and $Q^2$ is as defined for $R^3$ and $R^4$.

Alkoxy at $Q^3$ is as defined for R, R' and $R^1$.

Alkylene at W, X and Y is linear or branched alkylene having 1 to 6 carbon atoms, which is exemplified by methylene, ethylene, trimethylene, propylene, tetramethylene, pentamethylene, hexamethylene and the like.

Alkenylene at Y is linear or branched alkenylene having 2 to 6 carbon atoms, which is exemplified by vinylene, propenylene, butenylene, pentenylene and the like.

Alkyl at Rb is as defined for R, R' and $R^1$.

Aralkyl at Rb is as defined for R, R' and $R^1$.

Aminoalkyl at Rb is as defined for L.

Mono- or dialkylaminoalkyl at Rb is as defined for L.

The nitrogen-containing heteromonocycle at Rc is pyridine, pyrimidine, pyridazine, triazine, pyrazole, triazole and the like, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrrolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a]pyrimidine, 1H-pyrazolo[4,3-d]pyrimidine and the like), imidazopyrimidine (e.g., imidazo[1,2-a]pyrimidine, 1H-imidazo[4,5-d]pyrimidine and the like), pyrrolotriazine (e.g., pyrrolo[1,2-a]-1,3,5-triazine, pyrrolo[2,1-f]-1,2,4-triazine), pyrazolotriazine (e.g., pyrazolo[1,5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo[5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]pyrimidine, furo[3,2-d]pyrimidine and the like), 2,3-dihydropyrrolopyridine (e.g., 2,3-dihydro-1H-pyrrolo[2,3-b]pyridine, 2,3-dihydro-1H-pyrrolo[3,2-b]pyridine and the like), 2,3-dihydropyrrolopyrimidine (e.g., 2,3-dihydro-1H-pyrrolo[2,3-d]pyrimidine, 2,3-dihydro-1H-pyrrolo[3,2-d]pyrimidine and the like), 5,6,7,8-tetrahydropyrido[2,3-d]pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8dihydro-7-oxo-1,8-naphthyridine, 5,6,7,8-tetrahydro-7-oxo-1,8-naphthyridine and the like.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, alkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R, R' and $R^1$ and exemplified by methylhydrazino, ethylhydrazino, benzylhydrazino and the like.

The compound of the formula (I) is exemplified by the following compounds.

(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) 1-[3-(2-(2-thienylmethyl)phenoxy)-2-hydroxyproply]-4 (4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine
(9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)pyridine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1-methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyridylcarbamoyl)piperidine
(18) 1-(2-(4-methoxyphenyl)ethyl)-4-(4-pyridylcarbamoyl) piperidine
(19) 1-(2-(4-methoxyphenyl)ethyl)-4-(2-pyridylcarbamoyl) piperidine
(20) 1-(2-(4-chlorophenyl)ethyl)-4-(4-pyridylcarbamoyl) piperidine
(21) 1-diphenylmethyl-4-(2-pyridylcarbamoyl)piperidine
(22) 1-[2-(4-(5-methyl-3-oxo-2,3,4,5-tetrahydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)piperidine

(24) 1-(2-nitrophenyl)-4-(4-pyridylcarbamoyl)piperidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trimethoxybenzoyl)-4-(4-pyridylcarbamoyl)piperidine
(29) 1-acetyl-4-(4-pyridylcarbamoyl)piperidine
(30) 1-(3-(4-fluorobenzoyl)propyl)-4-(4-pyridylcarbamoyl)piperidine
(31) 1-(3-(4-fluorobenzoyl)propyl)-4-(2-pyridylcarbamoyl)piperidine
(32) 1-(1-(4-hydroxybenzoyl)ethyl)-4-(2-pyridylcarbamoyl)piperidine
(33) 1-(1-(4-benzyloxybenzoyl)ethyl)-4-(2-pyridylcarbamoyl)piperidine
(34) 1-(2-(4-hydroxyphenoxy)ethyl)-4-(2-pyridylcarbamoyl)piperidine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)piperidine
(39) 1-(2-hydroxy-3-phenoxypropyl)-4-(3-pyridylcarbamoyl)piperidine
(40) 1-(2-hydroxy-3-phenoxypropyl)-4-(2-pyridylcarbamoyl)piperidine
(41) 1-(2-phenylethyl)-4-[N-(2-pyridyl)-N-(2-(N,N-dimethylamino)ethyl)carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)piperidine
(44) 4-[N-(2-pyridyl)-N-(2-(N,N-dimethylamino)ethyl)carbamoyl]piperidine
(44) 4-[N-(2-pyridyl)-N-(2-(N,N-dimethylamino)ethyl)carbamoyl]piperidine
(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)piperidine
(48) 1-(6-chloro-2-methylimidazo[1,2-a]pyridine-3-carbonyl)-4-(4-pyridylcarbamoyl)piperidine
(49) 1-(4-nitrobenzyl)-4-(4-pyridylcarbamoyl)piperidine
(50) 1-hexyl-4-(4-pyridylcarbamoyl)piperidine
(51) 1-benzyloxycarbonyl-4-(2-chloro-4-pyridylcarbamoyl)piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)piperidine
(59) 4-(5-nitro-2-pyridylcarbamoyl)piperidine
(60) trans-4-benzyloxycarboxamidomethyl-1-(4-pyridylcarbamoyl)cyclohexane
(61) trans-4-aminomethyl-1-(4-pyridylcarbamoyl)cyclohexane
(62) trans-4-formamidomethyl-1-(4-pyridylcarbamoyl)cyclohexane
(63) trans-4-dimethylaminomethyl-1-(4-pyridylcarbamoyl)cyclohexane
(64) N-benzylidene-trans-(4-pyridylcarbamoyl)cyclohexylmethylamine
(65) trans-4-benzylaminomethyl-1-(4-pyridylcarbamoyl)cyclohexane
(66) trans-4-isopropylaminomethyl-1-(4-pyridylcarbamoyl)cyclohexane
(67) trans-4-nicotinoylaminomethyl-1-(4-pyridylcarbamoyl)cyclohexane
(68) trans-4-cyclohexylaminomethyl-1-(4-pyridylcarbamoyl)cyclohexane
(69) trans-4-benzyloxycarboxamide-1-(4-pyridylcarbamoyl)cyclohexane
(70) trans-4-amino-1-(4-pyridylcarbamoyl)cyclohexane
(71) trans-4-(1-aminoethyl)-1-(4-pyridylcarbamoyl)cyclohexane
(72) trans-4-aminomethyl-cis-2-methyl-1-(4-pyridylcarbamoyl)cyclohexane
(73) (+)-trans-4-(1-benzyloxycarboxamidopropyl)-1-cyclohexanecarboxylic acid
(74) (+)-trans-4-(1-benzyloxycarboxamidopropyl)-1-(4-pyridylcarbamoyl)cyclohexane
(75) (−)-trans-4-(1-benzyloxycarboxamidpropyl)-1-(4-pyridylcarbamoyl)cyclohexane
(76) (+)-trans-4-(1-aminopropyl)-1-(4-pyridylcarbamoyl)cyclohexane
(77) (−)-trans-4-(1-aminopropyl)-1-(4-pyridylcarbamoyl)cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)cyclohexane
(81) (−)-trans-4-(1-aminoethyl)-1-(4-pyridylcarbamoyl)cyclohexane
(82) trans-4-(4-chlorobenzoyl)aminomethyl-1-(4-pyridylcarbamoyl)cyclohexane
(83) trans-4-aminomethyl-1-(2-pyridylcarbamoyl)cyclohexane
(84) trans-4-benzyloxycarboxamidomethyl-1-(2-pyridylcarbamoyl)cyclohexane
(85) trans-4-methylaminomethyl-1-(4-pyridylcarbamoyl)cyclohexane
(86) trans-4-(N-benzyl-N-methylamino)methyl-1-(4-pyridylcarbamoyl)cyclohexane
(87) trans-4-aminomethyl-1-(3-pyridylcarbamoyl)cyclohexane
(88) trans-4-aminomethyl-1-[(3-hydroxy-2-pyridyl)carbamoyl]cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)cyclohexane
(94) 4-(trans-4-benzyloxycarboxamidomethylcyclohexylcarbonyl)-amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)cyclohexane

(97) trans-4-(1-benzyloxycarboxamidoethyl)-1-(4-pyridylcarbamoyl)cyclohexane
(98) trans-4-(1-amino-1-methylethyl)-1-(4-pyridylcarbamoyl)cyclohexane
(99) trans-4-(2-aminoethyl)-1-(4-pyridylcarbamoyl)cyclohexane
(100) trans-4-(2-amino-1-methylethyl)-1-(4-pyridylcarbamoyl)cyclohexane
(101) trans-4-(1-aminopropyl)-1-(4-pyridylcarbamoyl)cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethylcyclohexanecarboxamide
(108) trans-N-(1H-pyrrolo[2,3-b]pyridin-4-yl)-4-aminomethylcyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl)-4-(1-amino-1-methylethyl)cyclohexanecarboxamide
(111) trans-N-(1H-pyrazolo[3,4-b]pyridin-4-yl)-4-aminomethylcyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)-cyclohexanecarboxamide
(115) trans-N-(1H-pyrazolo[3,4-d]pyrimidin-4-yl)-4-aminomethylcyclohexanecarboxamide
(116) (+)-trans-N-(1H-pyrazolo[3,4-d]pyrimidin-4-yl)-4-(1-aminoethyl)cyclohexanecarboxamide
(117) trans-N-(1H-pyrazolo[3,4-d]pyrimidin-4-yl)-4-(1-amino-1-methylethyl)cyclohexanecarboxamide
(118) trans-N-(4-pyrimidinyl)-4-aminomethylcyclohexanecarboxamide
(119) trans-N-(3-amino-4-pyridyl)-4-aminomethylcyclohexanecarboxamide
(120) trans-N-(7H-imidazo[4,5-d]pyrimidin-6-yl)-4-aminomethylcyclohexanecarboxamide
(121) trans-N-(3H-1,2,3-triazolo[4,5-d]pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethylcyclohexanecarboxamide
(124) trans-N-(1H-pyrazolo[3,4-b]pyridin-4-yl)-4-aminomethylcyclohexanecarboxamide
(125) trans-N-(4-pyridazinyl)-4-aminomethylcyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethylcyclohexanecarboxamide
(128) trans-N-(thieno[2,3-d]pyrimidin-4-yl)-4-aminomethylcyclohexanecarboxamide
(129) trans-N-(5-methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(1-amino-1-methylethyl)cyclohexanecarboxamide
(132) trans-N-(2-(1-pyrrolidinyl)-4-pyridyl)-4-aminomethylcyclohexanecarboxamide
(133) trans-N-(2,6-diamino-4-pyrimidyl)-4-aminomethylcyclohexane-carboxamide
(134) (+)-trans-N-(7-methyl-1,8-naphthyridin-4-yl)-4-(1-aminoethyl)cyclohexanecarboxamide
(135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide
(138) trans-N-(2-azide-4-pyridyl)-4-aminomethylcyclohexanecarboxamide
(139) trans-N-(2,3-dihydro-1H-pyrrolo[2,3-b]pyridin-4-yl)-4-aminomethylcyclohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethylcyclohexanecarboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidinomethylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)cyclohexanecarboxamide
(151) trans-N-(1H-pyrrolo[2,3-b]pyridin-4-yl)-4-(3-phenylguanidinomethyl)cyclohexanecarboxamide
(152) trans-N-(1H-pyrrolo[2,3-b]pyridin-4-yl)-4-(3-propylguanidinomethyl)cyclohexanecarboxamide
(153) trans-N-(1H-pyrrolo[2,3-b]pyridin-4-yl)-4-(3-octylguanidinomethyl)cyclohexanecarboxamide
(154) trans-N-(1-benzyloxymethylpyrrolo[2,3-b]pyridin-4-yl)-4-(2-benzyl-3-ethylguanidinomethyl)cyclohexanecarboxamide
(155) trans-N-(1H-pyrrolo[2,3-b]pyridin-4-yl)-4-(imidazol-2-yl)aminomethylcyclohexanecarboxamide
(156) trans-N-(1H-pyrrolo[2,3-b]pyridin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pyridyl)-4-(1-aminoethyl)-3-nitrobenzamide
(162) (R)-(−)-N-(4-pyridyl)-3-amino-4-(1-aminoethyl)benzamide
(163) (R)-(+)-N-(4-pyridyl)-4-(1-aminoethyl)-3-chlorobenzamide
(164) N-(4-pyridyl)-3-aminomethylbenzamide (165) (R)-(+)-N-(1H-pyrrolo[2,3-b]pyridin-4-yl)-4-(1-aminoethyl)benzamide
(166) (R)-(+)-N-(1H-pyrazolo[3,4-b]pyridin-4-yl)-4-(1-aminoethyl)benzamide
(167) N-(1H-pyrazolo[3,4-b]pyridin-4-yl)-4-guanidinomethylbenzamide
(168) N-(4-pyridyl)-4-guanidinomethylbenzamide
(169) (R)-(+)-N-(4-pyridyl)-4-(1-aminoethyl)-3-fluorobenzamide
(170) N-(4-pyridyl)-4-aminomethylbenzamide
(171) N-(4-pyridyl)-4-aminomethyl-2-hydroxybenzamide
(172) N-(4-pyridyl)-4-(2-aminoethyl)benzamide
(173) N-(4-pyridyl)-4-aminomethyl-3-nitrobenzamide
(174) N-(4-pyridyl)-3-amino-4-aminomethylbenzamide
(175) (S)-(−)-N-(4-pyridyl)-4-(1-aminoethyl)benzamide
(176) (S)-(−)-N-(4-pyridyl)-2-(1-aminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzamide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitrobenzamide
(186) (R)-N-(1H-pyrazolo[3,4-b]pyridin-4-yl)-4-(1-guanidinoethyl)-3-nitrobenzamide
(187) (R)-N-(1H-pyrazolo[3,4-b]pyridin-4-yl)-4-(1-aminoethyl)-2-nitrobenzamide
(188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4-piperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-piperidinecarboxamide
(199) N-(1H-pyrrolo[2,3-b]pyridin-4-yl)-1-amidino-4-piperidinecarboxamide
(200) N-(1H-pyrrolo[2,3-b]pyridin-4-yl)-1-(3-phenylpropyl)-4-piperidinecarboxamide
(201) N-(1H-pyrrolo[2,3-b]pyridin-4-yl)-1-benzyl-4-piperidinecarboxamide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide Preferred are compounds (80), (109), (110), (112), (115), (142), (143), (144), (145), (153), (157), (163), (165), (166) and (179).

The compound having a Rho kinase inhibitory activity may be a pharmaceutically acceptable acid addition salt, wherein the acid is exemplified by inorganic acid such as hydrochloric acid, hydrobromic acid, sulfuric acid and the like, and organic acid such as methanesulfonic acid, fumaric acid, maleic acid, mandelic acid, citric acid, tartaric acid, salicylic acid and the like. A compound having a carboxylic group can be converted to a salt with a metal such as sodium, potassium, calcium, magnesium, aluminum and the like, a salt with an amino acid such as lysine and the like. Further, monohydrate, dihydrate, 1/2 hydrate, 1/3 hydrate, 1/4 hydrate, 2/3 hydrate, 3/2 hydrate, 6/5 hydrate and the like are encompassed in the present invention.

The compound of the formula (I) can be synthesized by a method described in, for example, JP-A-62-89679, JP-A-3-218356, JP-A-5-194401, JP-A-6-41080, WO95/28387, WO98/06433 and the like.

When the above-mentioned compound having a Rho kinase inhibitory activity has an optical isomer, its racemate or cis-trans isomers, all of them can be used in the present invention. These isomers can be isolated by a conventional method or can be produced using starting materials of the isomers.

A compound having a Rho kinase inhibitory activity, particularly, a compound of the formula (I), an isomer thereof and/or a pharmaceutically acceptable acid addition salt thereof have a preventive and therapeutic effect on interstitial pneumonia and pulmonary fibrosis in mammals inclusive of human, cow, horse, dog, mouse, rat and the like. Therefore, they can be used as an agent for the prophylaxis and treatment of various types of interstitial pneumonia and pulmonary fibrosis.

The agent for the prophylaxis and treatment of interstitial pneumonia and pulmonary fibrosis of the present invention is administered orally or parenterally.

For example, the compound having a Rho kinase inhibitory activity is mixed with a pharmaceutically acceptable carrier (e.g., excipient, binder, disintegrator, corrective, corrigent, emulsifier, diluent, solubilizer and the like) to give a pharmaceutical composition or a pharmaceutical preparation in the form of tablet, pill, powder, granule, capsule, troche, syrup, liquid, emulsion, suspension, injection (e.g., liquid, suspension and the like), suppository, inhalant, percutaneous absorber, eye drop, eye ointment and the like in the form suitable for oral or parenteral preparation.

When preparing a solid preparation, additives such as sucrose, lactose, cellulose sugar, D-mannitol, maltitol, dextran, starches, agar, arginates, chitins, chitosans, pectines, tragacanth gum, gum arabic, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethyleneglycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid paraffin and the like), wax (e.g., jojoba oil, carnauba wax, bee wax and the like), partly or entirely synthesized glycerol fatty acid esters (e.g., lauric acid, myristic acid, palmitic acid and the like), and the like are used.

Examples of commercially available products of these include Witepsol (manufactured by Dynamitnovel Ltd.), Farmazol (NOF Corporation) and the like.

When preparing a liquid preparation, an additive, such as sodium chloride, glucose, sorbitol, glycerol, olive oil, propylene glycol, ethyl alcohol and the like, is used. When preparing an injection, a sterile aqueous solution such as physiological saline, isotonic solution, oil (e.g., sesame oil and soybean oil) and the like are used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The eye drop can appropriately contain various additives such as buffer (borate buffer, acetate buffer, carbonate buffer and the like are preferable for reducing irritation), isotonicity agent, solubilizer, preservative, thickener, chelating agent, pH adjusting agent (generally, pH is preferably adjusted to about 6–8.5) and aromatic.

The dose of the compound having a Rho kinase inhibitory activity, which is the active ingredient of these preparations, is 0.1–100 wt %, suitably 1–50 wt %, of the preparation. While the dose varies depending on the symptom, body weight, age and the like of patients, it is generally about 1–500 mg a day for an adult, which is administered once to several times a day.

EXAMPLES

The present invention is explained in detail by referring to formulation examples and pharmacological action. The present invention is not limited in any way by the examples.

Formulation Example 1

Tablet

| | |
|---|---:|
| compound of the present invention | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention, lactose, corn starch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added. Using a $\phi$7 mm punch, tablets weighing 120 mg per tablet were prepared.

| | |
|---|---:|
| compound of the present invention | 10.0 mg |
| Lactose | 70.0 mg |
| Corn starch | 35.0 mg |
| Polyvinylpyrrolidone K30 | 2.0 mg |
| Talc | 2.7 mg |
| Magnesium stearate | 0.3 mg |
| | 120.0 mg |

The compound of the present invention, lactose and corn starch were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in hard capsules (No. 4) to give capsules weighing 120 mg.

The pharmacological action of the pharmaceutical agent of the present invention is explained in the following by referring to Experimental Examples.

In the following Experimental Examples, a compound having a Rho kinase inhibitory activity: (+)-trans-4-(1-aminoethyl)-1-(4-pyridylcarbamoyl)cyclohexane 2HCl.1H$_2$O (hereinafter Y-27632) was used. Y-27632 was dissolved and diluted in physiological saline to achieve a predetermined concentration.

Experimental Example 1

Expression of ROCK-II Gene in Bleomycin-induced Interstitial Pneumonia (Pulmonary Fibrosis) Model (Method)

Female C57BL/6 mice (about 15 g, 6-week-old) in 4 mice per group (n=4) were intraperitoneally administered with bleomycin 5 times a day every other day (total dose: 200 mg/kg) to prepare a model with bleomycin-induced interstitial pneumonia (pulmonary fibrosis).

The expression of ROCK-II gene in the lung at 7, 14, 21 and 40 days after the start of the bleomycin administration was measured, and so was the value of an animal free of bleomycin administration. The amount of the expression of the ROCK-II gene was measured according to a real time quantitative RT-PCR method. As the primer, the following sequence was used [forward: CATGGTGCATTGCGA-CACA (SEQ ID No. 1), reverse: TCGCCCATAGTAACAT-CACCT (SEQ ID No. 2)]. The amount of expression of the ROCK-II gene was expressed relatively in [(Rock-II m RNA)/(GAPDH m RNA)] using the expression amount of GAPDH (glyceraldehyde-3-phosphate dehydrogenase) gene as a standard. The results are shown in mean±SEM (n=4). For the test, (Satical analysis was performed One-way ANOVA test followed by Fisher's least significance test) was performed.

(Results)

The expression amount of ROCK-II gene of the bleomycin administration group was significantly high at day 7 and day 21 as compared to the bleomycin non-administration group (FIG. 1). Particularly, it increased to about 9 times the amount of the bleomycin non-administration group at day 21.

Experimental Example 2

Effect in Bleomycin-induced Interstitial Pneumonia (Pulmonary Fibrosis) Model

Using the bleomycin-induced interstitial pneumonia (pulmonary fibrosis) model prepared in Experimental Example 1, the effect of the present invention on induced interstitial pneumonia (pulmonary fibrosis) was examined.

(Method)

Y-27632 was intraperitoneally administered immediately before bleomycin administration from the first day of bleomycin administration (0th) to day 8 (5th administration), and thereafter until day 40, by way of a single, alternate-day administration. At day 40, the level of fibrosis was checked by hydroxyproline content and tissue staining. The hydroxyproline content was measured according to the report of Tran et al. (Tran et al., J. Clin. Invest., 99: 608–617, 1997). The degree of fibrosis by tissue staining was evaluated by the Aschcroft score (Aschcroft et al., J. Clin. Pathol., 41: 467–70, 1988).

(Results)

1. Hydroxyproline Content

Y-27632 dose-dependently suppressed the increase of hydroxyproline content due to bleomycin administration (Table 1). The suppression percentage was calculated based on the bleomycin alone administration group as 0% suppression, and the physiological saline administration group as 100% suppression.

TABLE 1

|  | Suppression (%) |
|---|---|
| bleomycin + Y-27632 (100 μg/kg) | 53.8 |
| + Y-27632 (10 μg/kg) | 38.6 |
| + Y-27632 (1 μg/kg) | 30.0 |
| + Y-27632 (0.1 μg/kg) | 28.2 |
| + Y-27632 (0.01 μg/kg) | −10.6 |
| Y-27632 alone (1000 μg/kg) | 92.1 |

2. Measurement of Pulmonary Fibrosis Level by Tissue Staining

Y-27632 suppressed the increase of Aschcroft score due to bleomycin administration at the dose of not less than 10 μg/kg (Table 2). In the Table, *:p<0.05, **:p<0.01.

TABLE 2

|  | Aschcroft score (mean ± standard error) |
|---|---|
| bleomycin alone | 3.54 ± 0.43 |
| bleomycin + Y-27632 (0.1 μg/kg) | 2.79 ± 0.26 |
| + Y-27632 (10 μg/kg) | 1.85 ± 0.26** |
| + Y-27632 (100 μg/kg) | 1.98 ± 0.41* |
| Y-27632 alone (1000 μg/kg) | 1.33 ± 0.21 |
| physiological saline administration group | 1.12 ± 0.32 |

Experimental Example 3
Effect on the Number of Inflammatory cells in Bronchoalveolar Lavage Fluid (BALF) in Bleomycin-induced Interstitial Pneumonia (Pulmonary Fibrosis) Model
(Method)

Using the pulmonary fibrosis model administered with bleomycin as in Experimental Example 1, the effect of Y-27632 on the number of various inflammatory cells in BALF was examined.

The dose of Y-27632 was administered every other day at the lo dose of 100 μg/kg in the same manner as in Experimental Example 2. BALF was recovered at day 7, day 14, day 21 and day 40 from the start of the bleomycin administration, and the number of total cells, macrophages, lymphocytes and neutrophils was counted (n=5). The number of total cells was measured by a hemocytometer. Smear preparations of the various cells in BALF were prepared by cytospin (Auto Smer CF-12D, Chiyoda seisakusho, Tokyo, Japan), stained with May-Gruenwald and subjected to the counting under a microscope.
(Results)

Figure 2:
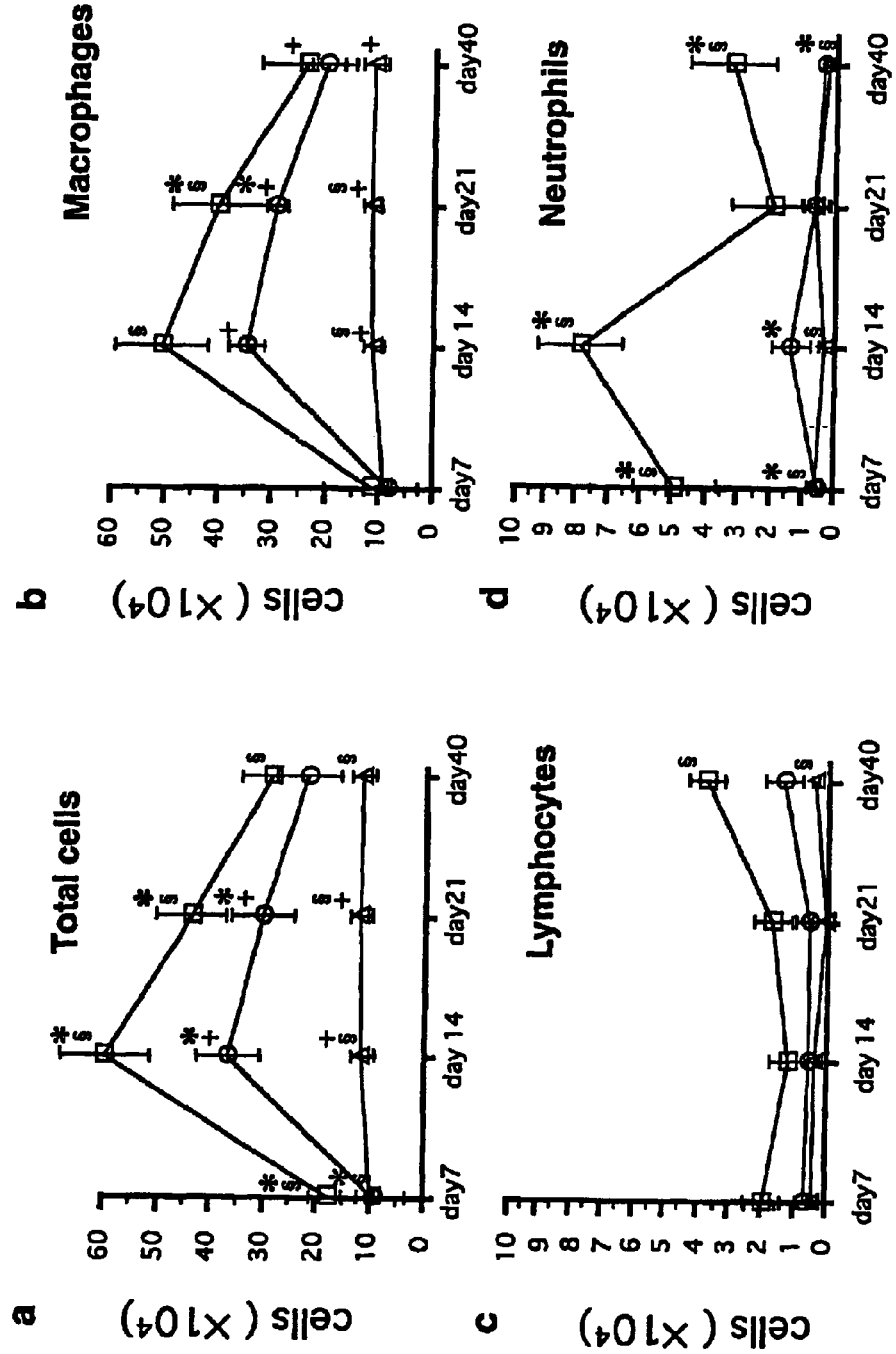
FIG. 2 is a graph showing the effect of the compound of the present invention (Y-27632) on the number of inflammatory cells in bronchoalveolar lavage of a model with bleomycin-induced interstitial pneumonia (pulmonary fibrosis), wherein the axis of ordinates shows the number of cells of respective kinds of inflammatory cells, the axis of abscissas shows the time (days) after bleomycin administration, □ shows a group (BLM group) administered with bleomycin and physiological saline every other day, ○ shows a group (Y-27632 group) administered with bleomycin and Y-27632 every other day, and Δ shows a group (Normal group) not administered with bleomycin but with physiological saline every other day (n=5, *p<0.05; BLM group vs Y-27632 group, § p<0.05; BLM group vs Normal group, +p<0.05; Y-27632 group vs Normal group).

The results are shown in FIG. 2, wherein □ shows a group (BLM group) subjected to bleomycin administration and alternate-day administration of physiological saline, ○ shows a group (Y-27632 group) subjected to bleomycin administration and alternate-day administration of Y-27632, and Δ shows a group (Normal group) subjected to alternate-day administration of physiological saline but without bleomycin administration. The results are shown in mean±SEM (n=5). For the test, (Satical analysis was performed One-way ANOVA test followed by Fisher's least significance test) was performed (*p<0.05; BLM group vs Y-27632 group) (§p<0.05; BLM group vs Normal group) (+p<0.05; Y-27632 group vs Normal group).

The lymphocyte (c) counts did not show a significant difference among 3 groups. The Y-27632 group showed significantly lower results than BLM group in the number of total cells (a), macrophages (b) and neutrophils (d).

Therefrom it was clarified that the treatment with Y-27632 suppresses infiltration of inflammatory cells into BALF.

Experimental Example 4
Effect on Cell Chemotaxis
(Results)

Mouse alveolar macrophage-derived cell line (MH-S cell), fibroblast (NIH3T3 cell) and mouse neutrophil were used. Casein was intraperitoneally administered to the mouse and the mouse neutrophil was isolated from ascites thereof after 6 h. The cell chemotaxis was measured by a Boyden chamber (chemotaxicell, KURABO, Japan). The pore size of the filter used was 5 μm for MH-S cell and neutrophil, and 8 μm for NIH3T3 cell. As a chemotactic factor, lipopolysaccharide (LPS, $E.coli$: B-4, Sigma, St Louis, Mo., USA) was used for MH-S cell, mouse interleukin 1β (IL-1β, Genzyme/techne, USA) was used for neutrophil, and a platelet activating factor (PDGF-BB, UBI, Lake Placid, USA) was used for NIH3T3 cell. The chemotactic factors were added to a lower layer and Y-27632 were added to a higher layer at various concentrations. The reaction was carried out at 37° C. for 120 min for MH-S cell and NIH3T3 cell and 37° C. for 90 min for neutrophil. After the completion of the reaction, migrated cells were stained with Giemsa (Muto, CO., Ltd, Japan) and the cells were counted. The value is in mean±SEM.
(Results)

Figure 3:
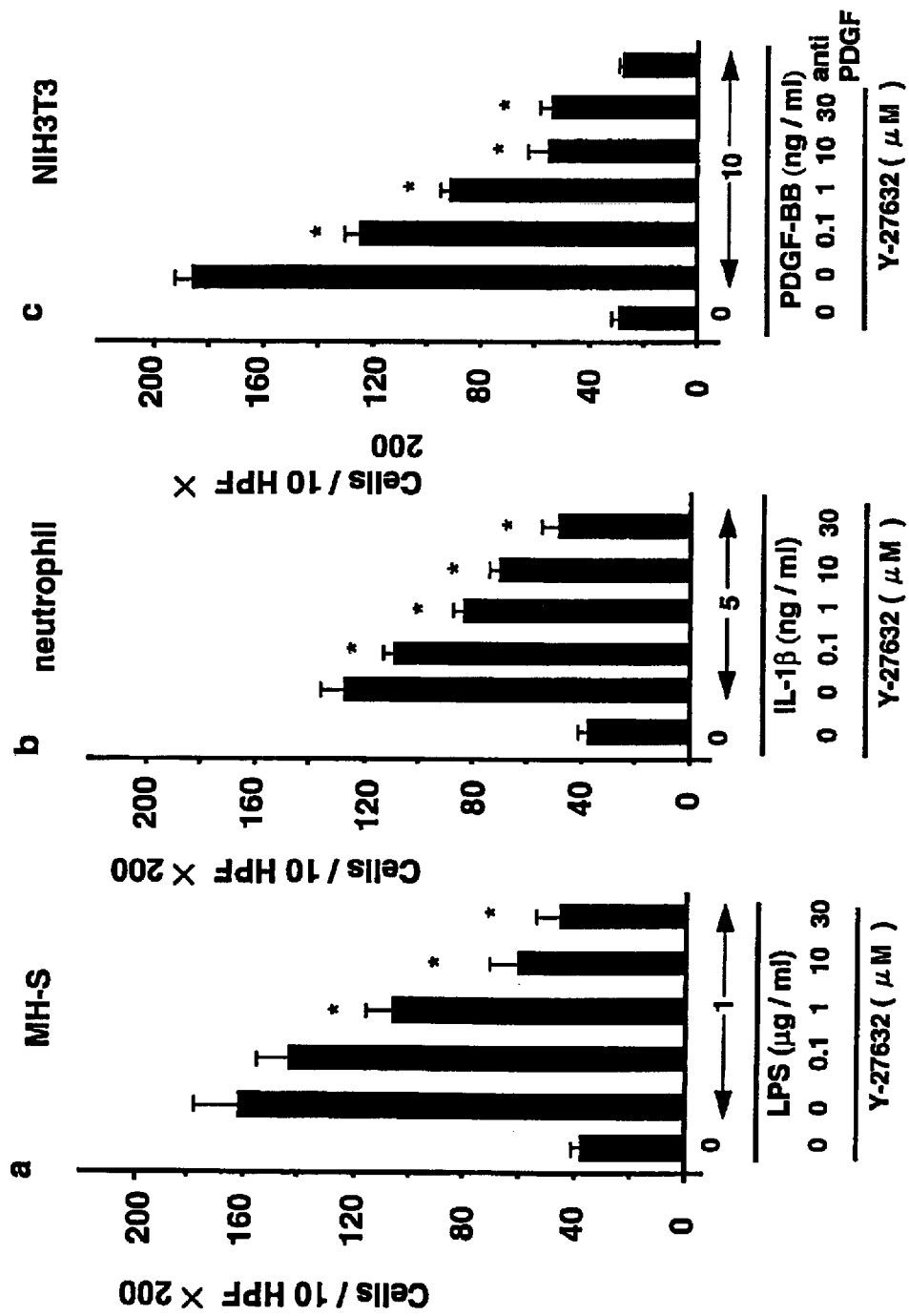
FIG. 3 is a graph showing the action of the compound of the present invention (Y-27632) on cell chemotaxis, wherein the axis of ordinates shows the number of migrated cell and the axis of abscissas shows the concentration of Y-27632 (n=6, *p<0.05 Y-27632-untreated group vs Y-27632-treated group).

In MH-S cells, Y-27632 suppressed the migration by LPS (1 μg/ml) in a concentration-dependent manner, and the $IC_{50}$ value thereof was 4.8±2.0 μM (n=6) (FIG. 3($a$)). In neutrophils, Y-27632 suppressed the migration by IL-1. (5 ng/ml) in a concentration-dependent manner and the $IC_{50}$ value thereof was 8.4±2.1 μM (n=6) (FIG. 3($b$)). In NIH3T3 cells, Y-27632 suppressed the migration by PDGF-BB (10 ng/ml) in a concentration-dependent manner, and the $IC_{50}$ value thereof was 1.6±0.5 μM (n=6) (FIG. 3($c$)).

INDUSTRIAL APPLICABILITY

From the above-mentioned Formulation Example and Experimental Example and pharmacological tests, it is clear that a compound having a Rho kinase inhibitory activity shows a preventive and therapeutic effect on interstitial pneumonia and pulmonary fibrosis, and is useful as an agent for the prevention and treatment of interstitial pneumonia and pulmonary fibrosis.

The bleomycin-induced interstitial pneumonia (pulmonary fibrosis) model used in the present invention showed a significantly higher expression amount of ROCK-II gene, and activation of the ROCK-II gene was suggested to be involved in the expression of interstitial pneumonia and pulmonary fibrosis.

Moreover, it was confirmed that the compound having a Rho kinase inhibitory activity of the present invention suppresses infiltration of various inflammatory cells into tracheal alveolar, and at the same time, suppresses migration of each cell of macrophage-derived cell, fibroblast and neutrophil, in the bleomycin-induced interstitial pneumonia (pulmonary fibrosis) model used in the present invention.

This application is based on a patent application No. 81072/1999 filed in Japan, the content of which is hereby incorporated by reference.

SEQUENCE LISTING FREE TEXT

SEQ ID NO: 1: Oligonucleotide designed to act as sequencing primer (forward).
SEQ ID NO: 2: Oligonucleotide designed to act as sequencing primer (reverse).

What is claimed is:

1. A method for treatment of interstitial pneumonia and pulmonary fibrosis, which comprises administering an effective amount of a compound having a Rho kinase inhibitory activity to a patient, wherein the compound having a Rho kinase inhibitory activity is an amide compound of the following formula (I),

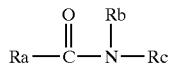

(I)

wherein

Ra is a group of the formula

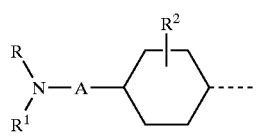

(a)

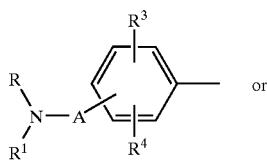

(b)

or

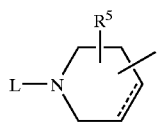

(c)

in the formulas (a) and (b),

R is hydrogen, alkyl, or cycloalkyl, cycloalkylalkyl, phenyl or aralkyl, which optionally has a substituent on the ring, or a group of the formula

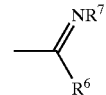

(d)

wherein $R^6$ is hydrogen, alkyl or the formula: —$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

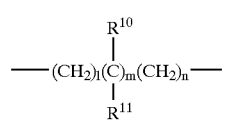

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

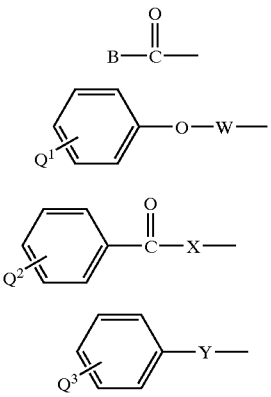

(f)

(g)

(h)

or (i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

2. The method for treatment of interstitial pneumonia and pulmonary fibrosis of claim 1, wherein the compound having a Rho kinase inhibitory activity is an amide compound of the following formula (I')

(I')

wherein

Ra' is a group of the formula

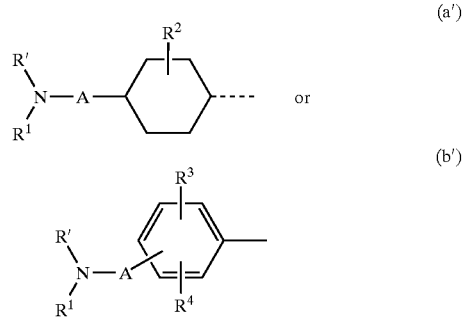

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

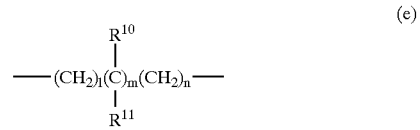

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

3. The method for treatment of interstitial pneumonia and pulmonary fibrosis of claim 1, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4- -(1-aminoethyl)cyclohexanecarboxamide, (R)-(+)-N-(4-pyridyl)-4(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

4. The method for treatment of interstitial pneumonia and pulmonary fibrosis of claim 1, wherein the compound having a Rho kinase inhibitory activity is a (+)-trans-4-(1- aminoethyl)-1-(4-pyridylcarbamoyl)cyclohexane, and/or a pharmaceutically acceptable acid addition salt thereof.

5. A method for the production of an agent for treatment of interstitial pneumonia and pulmonary fibrosis, which comprises mixing a compound having a Rho kinase inhibitory activity with a pharmaceutically acceptable carrier, wherein the compound having a Rho kinase inhibitory activity is an amide compound of the following formula (I)

(I)

wherein
Ra is a group of the formula

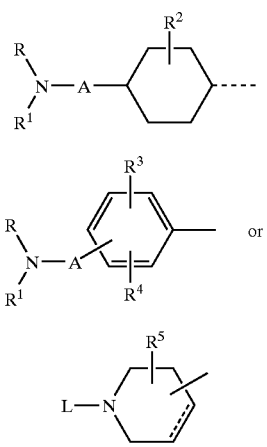

in the formulas (a) and (b),
R is hydrogen, alkyl, or cycloalkyl, cycloalkylalkyl, phenyl or aralkyl, which optionally has a substituent on the ring, or a group of the formula

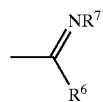

(d)

wherein $R^6$ is hydrogen, alkyl or formula: —$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

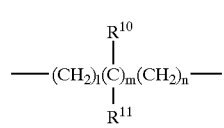

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

(f)

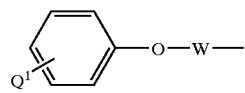

(g)

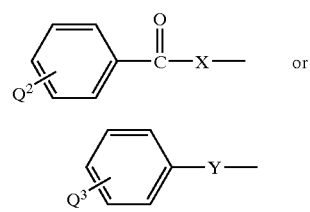

(h)

(i)

wherein
B is hydrogen, alkyl, alkoxy, aralkyl, aralkyloxy, aminoalkyl, hydroxyalkyl, alkanoyloxy-alkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

6. The method of claim 5, wherein the compound having a Rho kinase inhibitory activity is an amide compound of the following formula (I')

A is a group of the formula

 (I')

wherein
Ra' is a group of the formula

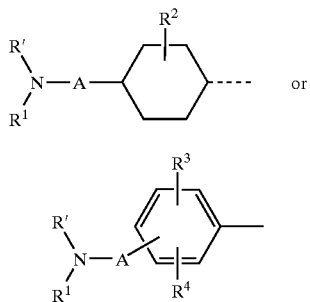

wherein
R' is hydrogen, alkyl, or cycloalkyl, cycloalkylalkyl, phenyl or aralkyl, which optionally has a substituent on the ring,
$R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally having, in the ring, oxygen atom, sulfur atom or optionally substituted nitrogen atom,
$R^2$ is hydrogen or alkyl,
$R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula

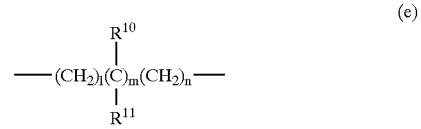 (e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

7. The method of claim 5, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

8. The method of claim 5, wherein the compound having a Rho kinase inhibitory activity is a (+)-trans-4-(1-aminoethyl)-1-(4-pyridylcarbamoyl)cyclohexane, and/or a pharmaceutically acceptable acid addition salt thereof.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide designed to act as forward
      sequencing primer.

<400> SEQUENCE: 1
catggtgcat tgcgacaca                                                   19

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide designed to act as reverse
      sequencing primer.

<400> SEQUENCE: 2
tcgcccatag taacatcacc t                                                21
```